United States Patent [19]

Blaser et al.

[11] Plant 5,072

[45] Jul. 19, 1983

[54] CALLISTEMON 'BOYETTE'

[76] Inventors: John A. Blaser, 7605 N. Tuttle Ave.; Robert J. Boyette, 2340 Tallevast Rd., both of Sarasota, Fla. 33581

[21] Appl. No.: 324,676

[22] Filed: Nov. 24, 1981

[51] Int. Cl.[3] ..... A01H 5/00
[52] U.S. Cl. ..... Plt./54
[58] Field of Search ..... Plt./54

[56] References Cited

U.S. PATENT DOCUMENTS

P.P. 3,674 1/1975 Tasche ..... Plt./54

*Primary Examiner*—James R. Feyrer
*Attorney, Agent, or Firm*—LeBlanc, Nolan, Shur & Nies

[57] ABSTRACT

There is disclosed a new and distinct variety of Callistemon, characterized by an extreme weeping habit and persistent year-round flowering.

2 Drawing Figures

1

FIELD OF THE INVENTION

This invention relates to a new and distinct plant variety of *Callistemon viminalis,* which is a member of the Myrtaceae family.

BACKGROUND OF THE INVENTION

*Callistemon viminalis* has been grown for many years as an ornamental flowering tree for use in landscaping.

The instant variety which we discovered among plants growing on property in Tallevast, Fla. was closely observed from the time we first found the same and its distinctive characteristics made it stand out from other *Callistemon viminalis* growing nearby.

During the natural course of production of *Callistemon viminalis* at a nursery in Tallevast, Fla., cuttings were selected from the best stock in the field with the thought of improving the variety. By this process, the instant sport was selected because of its extreme weeping characteristic and persistent year-round flowering. Its growth habit is unusually much different from the parent plant, having a much more extreme weeping habit than the parent and also being a much more persistent bloomer, blooming on a year-round basis while the parent *Callistemon viminalis* blooms fall and spring only, with a more pronounced flowering in the spring. Such characteristics enhance the beauty of this new variety. We have named the selection *Callistemon viminalis* "Boyette".

This new variety has been asexually reproduced from cuttings at a nursery in Tallevast, Fla., and its distinguishing characteristics have proven to be permanent.

DESCRIPTION OF THE DRAWINGS

The accompanying drawings serve by color photographic means to illustrate the new variety, one sheet showing an entire tree of the new variety, having a height of approximately ten feet, while the other sheet provides a photographic close-up of the weeping branches of the new variety with details of the blossom clusters and leaves.

2

DETAILED DESCRIPTION OF THE NEW VARIETY

The following is a detailed description of the new variety *Callistemon viminalis* "Boyette", with color terminology in accordance with the chart "Exotica Horticultural Color Guide" published in *Exotica 3.*

Parentage: A sport of *Callistemon viminalis.*

Propagation: Holds its distinguishing characteristics through successive propagation from cuttings and roots.

Plant:

*Form.*—Small evergreen tree having extreme weeping habit, similar to that of a weeping willow.

*Height.*—Grows to 16 to 20 feet at maturity.

Foliage:

*Size of leaf.*—One to two inches long and ¼ to ½ inches wide, in the mature leaf, with a short petiole.

*Shape of leaf.*—Small narrow leaves typical of the species. The leaves are simple, alternate, entire. The leaves are rigid and when crushed have a camphor-like odor.

Flower:

*Blooming habit.*—Profuse and recurrent the year around.

*Size.*—The blossom cluster will vary from 3 to 6 inches long and from 2 to 2¼ inches in diameter.

*Shape.*—The shape of the blossom cluster is almost an exact duplicate of a test tube brush.

*Color.*—The flower color is cherry.

This new variety of *Callistemon viminalis* is particularly attractive as an ornamental landscaping specimen. It is vigorous in growth habit, producing a dense array of weeping branches having an extreme weeping habit. The profuse and year-round recurrent blooming habit of this new variety also adds to its overall attractiveness and commercial value.

It is claimed:

1. The new and distinct variety of *Callistemon viminalis,* substantially as herein shown and described, characterized particularly as to novelty by an extreme weeping habit and persistent year-round blooming.

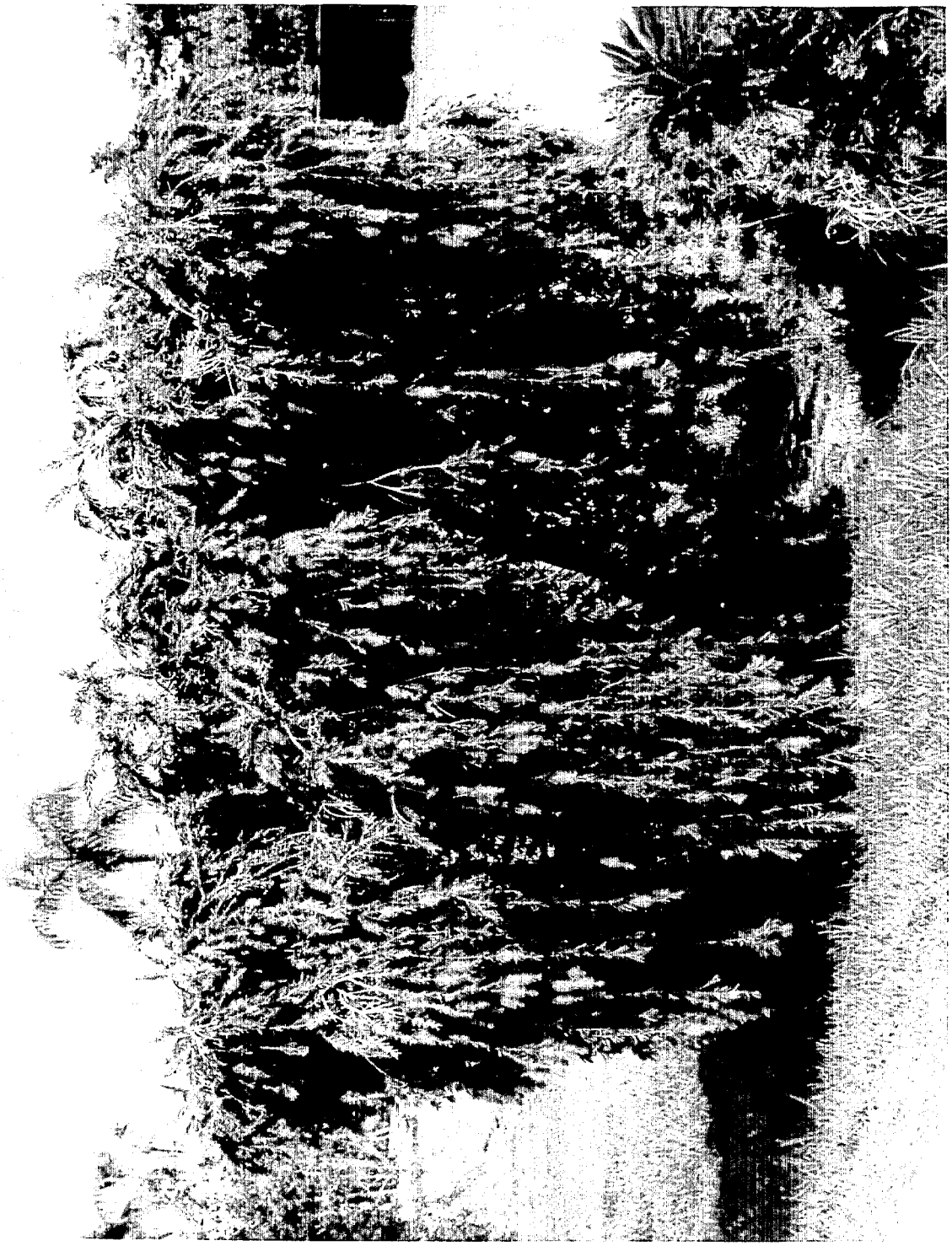

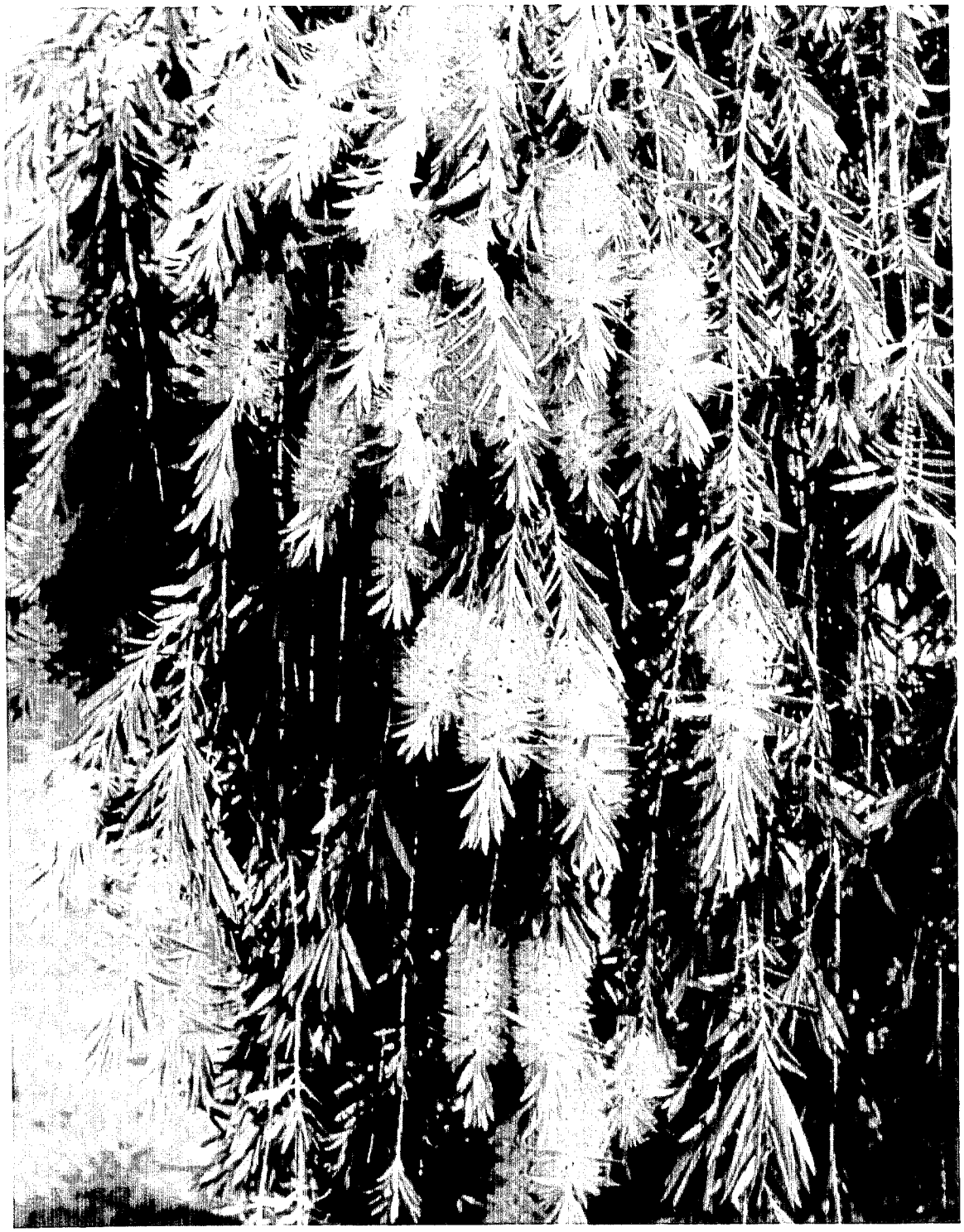

* * * * *